(12) United States Patent
Seok et al.

(10) Patent No.: US 8,549,929 B2
(45) Date of Patent: Oct. 8, 2013

(54) COMPACT PIPE SPECIMEN

(75) Inventors: Chang Sung Seok, Gwacheon-si (KR);
Sung Keun Cho, Seoul-si (KR); Haeng Cheol Cho, legal representative, Seoul-si (KR); Kwang Sang Seon, Jeollanam-do (KR); Kwang Hyeon Lee, Suwon-si (KR); Soo Park, Iksan-si (KR)

(73) Assignee: Sungkyunkwan University Foundation for Corporate Collaboration (KR)

( * ) Notice: Subject to any disclaimer, the term of this patent is extended or adjusted under 35 U.S.C. 154(b) by 298 days.

(21) Appl. No.: 12/747,758

(22) PCT Filed: Oct. 31, 2008

(86) PCT No.: PCT/KR2008/006449
§ 371 (c)(1),
(2), (4) Date: Dec. 6, 2010

(87) PCT Pub. No.: WO2009/075475
PCT Pub. Date: Jun. 18, 2009

(65) Prior Publication Data
US 2011/0094307 A1    Apr. 28, 2011

(30) Foreign Application Priority Data

Dec. 12, 2007    (KR) .................. 10-2007-0128751

(51) Int. Cl.
*G01N 3/20*    (2006.01)
(52) U.S. Cl.
USPC .......................................................... 73/851
(58) Field of Classification Search
USPC .......................................................... 73/851
See application file for complete search history.

(56) References Cited

U.S. PATENT DOCUMENTS

| 3,482,437 | A | * | 12/1969 | Martens | 73/799 |
| 4,116,049 | A | * | 9/1978 | Barker | 73/87 |
| 4,895,027 | A | * | 1/1990 | Manahan, Sr. | 73/799 |
| 4,916,954 | A | * | 4/1990 | Buzzard | 73/799 |
| 5,598,738 | A | * | 2/1997 | Buescher et al. | 73/761 |
| 6,532,825 | B1 | * | 3/2003 | Abe | 73/804 |

FOREIGN PATENT DOCUMENTS

| JP | 55-142236 | 11/1980 |
| JP | 60-140147 | 7/1985 |
| JP | 2002-267581 | 9/2002 |
| KR | 10-2004-0044658 | 5/2004 |

OTHER PUBLICATIONS

"Standard Test Method for Measurement of Fracture Toughness," ASTM International, vol. 03.01, Aug. 2001, pp. 1-46.
International Search Report—PCT/KR2008/006449 dated Feb. 26, 2009.

* cited by examiner

*Primary Examiner* — Lisa Caputo
*Assistant Examiner* — Octavia D. Hollington
(74) *Attorney, Agent, or Firm* — Cantor Colburn LLP (57) ABSTRACT

A compact pipe specimen applicable to a fracture toughness test used to evaluate physical properties of a pipe material is provided. The compact pipe specimen includes: a pipe having a notch portion formed in a circumferential direction and a crack portion formed at the edge of the notch portion; and first and second jigs having openings to which a pressurizing unit is coupled so as to cause a bending load on the pipe, having the notch portion therebetween, and attached to the exterior surface of the pipe, respectively. It is unnecessary to correct the influence of a constraint effect due to varying sizes and shapes of the specimen. There is no restriction to the curvature and thickness of a pipe. A fracture behavior of a pipe crack portion can be precisely simulated.

15 Claims, 7 Drawing Sheets

*Prior Art*

Fig. 8

*Prior Art*

COMPACT PIPE SPECIMEN

TECHNICAL FIELD

The present invention relates to a compact pipe specimen, and more particularly, to a compact pipe specimen applicable to a fracture toughness test which is used to evaluate physical properties of a pipe material.

BACKGROUND ART

It is necessary to obtain a fracture characteristic value of a pipe structure in order to apply leak before break (LBB) analysis results to the pipe structure so as to prevent problems, such as an accident occurring at a nuclear power plant. However, a great number of pipes and test devices are used to obtain the fracture characteristic value of the pipe structure, which is costly and takes much time, making it very difficult to conduct a proof test.

Therefore, rather than using a large number of pipes and test devices, a method of obtaining a fracture characteristic value of a material through a standard specimen test, analyzing the pipe structure based on the fracture characteristic value, and evaluating the fracture characteristics has been suggested.

The Standard Test Method for Measurement of Fracture Toughness (ASTM E1820) provides the size and shape of a compact tension (CT) specimen or a single edge notched bending (SENB) specimen that are standard specimens suggested by the American Society for Testing and Materials (ASTM). In more detail, referring to FIG. 7, a CT specimen 600 is in a rectangular planar shape. A mechanically processed notch portion 612 is formed in one side of the CT specimen 600. A crack portion 614 is formed at the edge of the notch portion 612. Two openings 618 and 619 are formed in the upper and lower portions of the CT specimen 600. The notch portion 612 is disposed between the openings 618 and 619. A bending load is applied to the openings 618 and 619 by using a pressurizing unit such as a pin, thereby obtaining the fracture characteristic value of the material.

Figure 8:
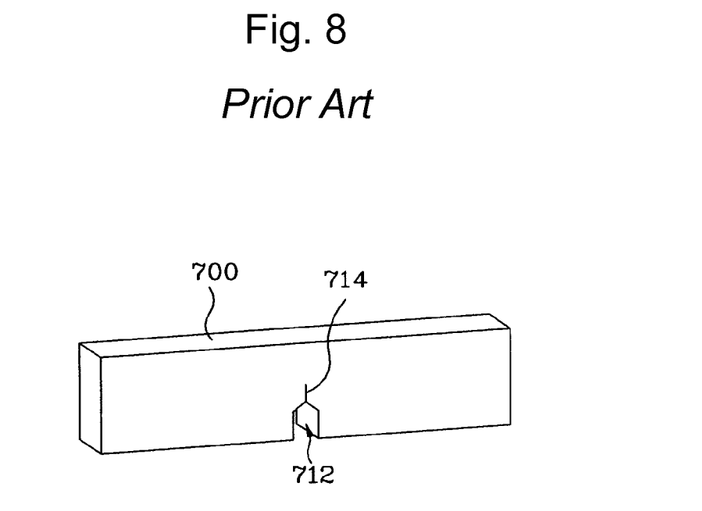
FIG. 8 is a perspective view of a conventional single edge notched bending (SENB) specimen.

Referring to FIG. 8, an SENB specimen 700, which has a mechanically processed notch portion 712 and a crack portion 714 formed at the edge of the notch portion 712 is applied. A bending load is applied to the SENB specimen 700, and the fracture value of the material is obtained.

As described above, although there is an advantage in that the conventional standard specimen has a standard specimen shape and testing method, specimen manufacture is restricted in terms of the curvature and thickness of a pipe.

Furthermore, the fracture characteristic value should be obtained in consideration of a constraint effect of a geometrical shape or size of the specimen, and the pipe structure is greatly influenced by the constraint effect. Therefore, although the standard specimen is used to conduct a test, it is necessary to compensate for the influence of the constraint effect due to varying sizes and shapes of pipes to be actually used.

Figure 7:
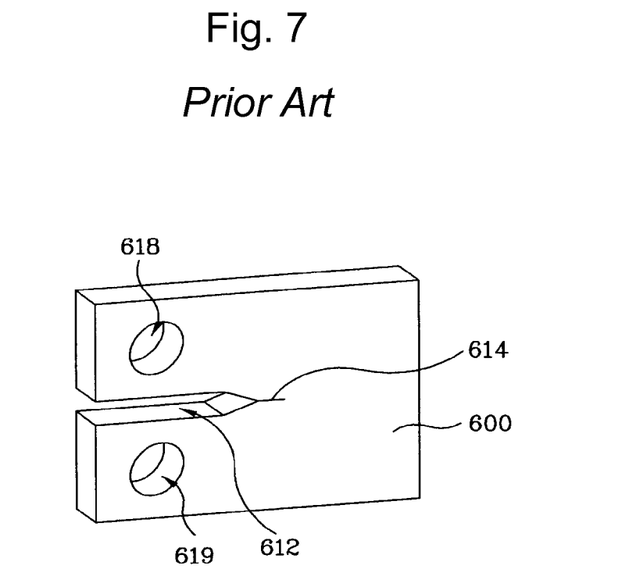
FIG. 7 is a perspective view of a conventional compact tension (CT) specimen.

Moreover, it is difficult to process the conventional CT specimen shown in FIG. 7 due to the complicated shape thereof, and the conventional SENB specimen shown in FIG. 8 consumes a great amount of materials despite being easily processed.

DISCLOSURE OF INVENTION

Technical Problem

The present invention provides a compact pipe specimen that does not need to compensate for the influence of a constraint effect due to varying sizes and shapes of the pipe specimen and is not restricted by the curvature and thickness of the pipe.

The present invention also provides a compact pipe specimen that needs a simple test facility and precisely simulates fracture behavior of a pipe crack portion.

Technical Solution

According to an aspect of the present invention, there is provided a compact pipe specimen applicable to a fracture toughness test of a pipe material, the compact pipe specimen comprising: a pipe having a notch portion formed in a circumferential direction and a crack portion formed at the edge of the notch portion; and first and second jigs having openings to which a pressurizing unit is coupled so as to cause a bending load on the pipe, having the notch portion therebetween, and attached to the exterior surface of the pipe, respectively.

The arm lengths of the first and second jigs may be adjusted according to the thickness of the pipe in a radial direction of the pipe. The openings may be in the form of slots extending in a lengthwise direction of the first and second jigs.

Projections may be formed toward the pipe on the first and second jigs that are attached to the pipe, respectively, wherein holes are formed in the pipe, pass through the pipe in the radial direction of the pipe, and have sizes corresponding to the cross-sections of the projections, and wherein the projections are coupled to the holes so that the first and second jigs are attached to the exterior surface of the pipe, respectively.

End portions of the projections coupled to the holes may be coupled to engagement units inside the pipe. The engagement units may include washers and bolts, wherein the end portions of the projections are processed into nuts and are coupled to the washers and bolts.

The engagement units may include washers and nuts, wherein the end portions of the projections are processed into bolts and are coupled to the washers and nuts.

A weight may be attached to the edge of the first jig or the second jig.

The exterior surface of at least one of the first and second jigs and the pipe may be processed so that the first jig and the pipe or the second jig and the pipe have contact surfaces matching each other. A plane portion may be formed on the exterior surface of the pipe to which the first jig or the second jig is attached.

Advantageous Effects

Since the size and shape of a pipe applied to a fracture toughness test are the same as those of an actually used pipe, the compact pipe specimen does not need to compensate for the influence of a constraint effect due to varying sizes and shapes of the pipe.

A jig, which is not influenced by the curvature of the pipe, is directly attached to the exterior surface of the pipe, and causes a large bending load on the pipe due to a small load generated by pins.

The length of an arm of the jig is adjusted according to the thickness of the wall of the pipe in a radial direction, which causes the large bending load on the pipe due to the small load generated by pins, so that a fracture toughness test of the pipe can be conducted by using a relatively small capacity of a test device.

The compact pipe specimen is not restricted by the curvature and thickness of the pipe, and thus a fracture characteristic value with regard to pipes having a variety of curvatures and thicknesses can be obtained.

The compact pipe specimen needs a miniaturized and simplified test facility compared to the conventional specimen and tests can be conducted in a laboratory, making it possible to conduct a test at a high temperature, for example, to simulate actual operating conditions of a nuclear reactor.

BEST MODE FOR CARRYING OUT THE INVENTION

The present invention will now be described more fully with reference to the accompanying drawings, in which exemplary embodiments of the invention are shown. This invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. Like reference numerals in the drawings denote like elements, and thus their description will be omitted.

Figure 1:
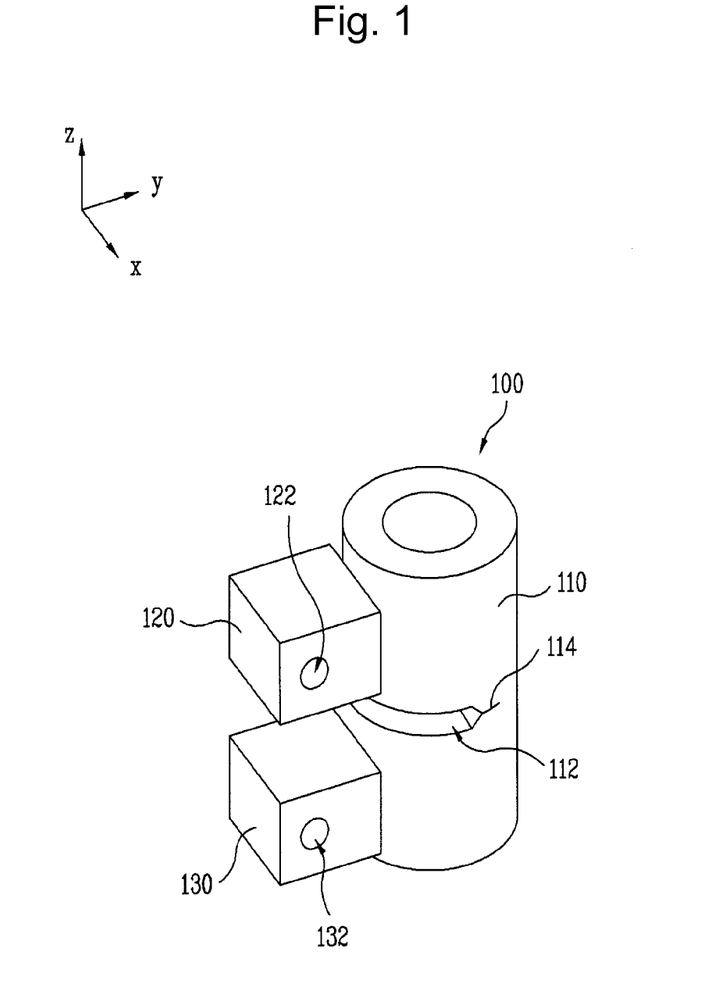
FIG. 1 is a perspective view of a compact pipe specimen having a pipe and first and second jigs that are attached to the pipe according to an embodiment of the present invention.
Figure 2:
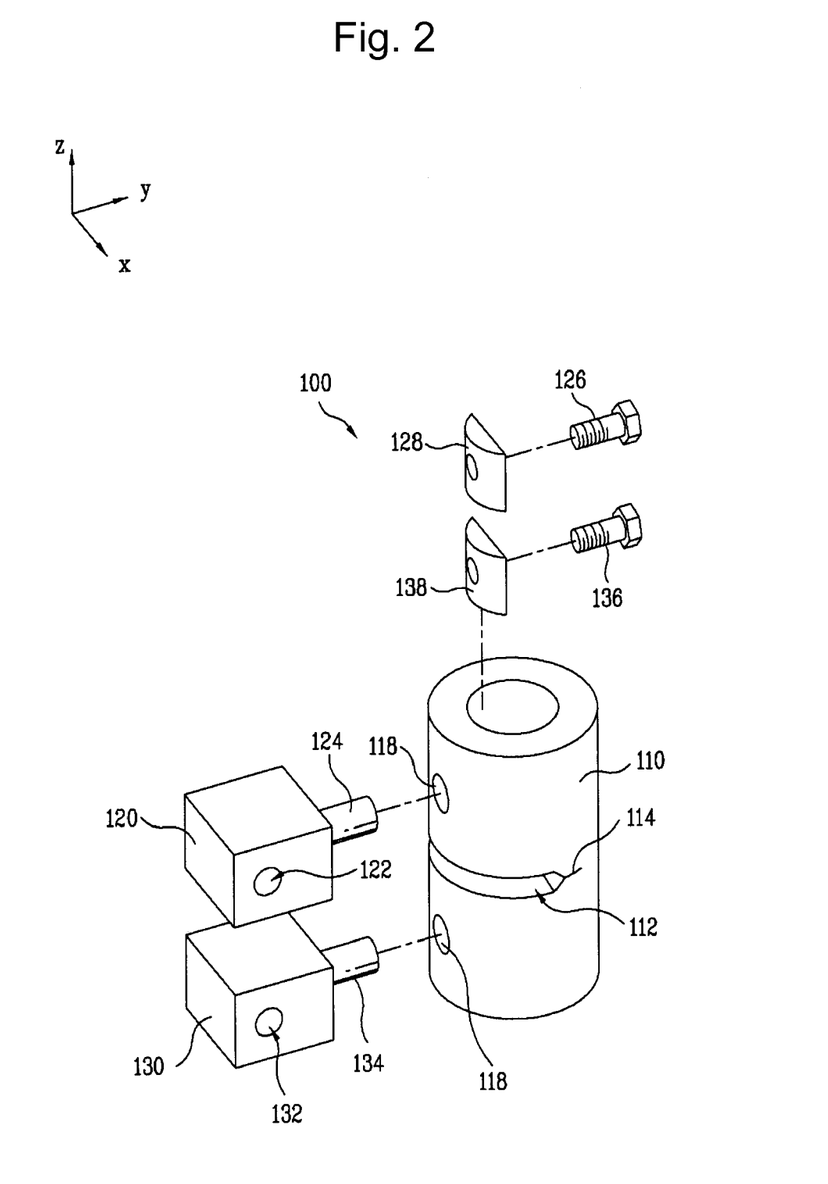
FIG. 2 is an exploded perspective view of the compact pipe specimen having the pipe and the first and second jigs that are separated from each other according to an embodiment of the present invention.

FIG. 1 is a perspective view of a compact pipe specimen 100 having a pipe 110 and first and second jigs 120 and 130 that are attached to the pipe 110 according to an embodiment of the present invention. FIG. 2 is an exploded perspective view of the compact pipe specimen 100 having the pipe 110 and the first and second jigs 120 and 130 that are separated from each other according to an embodiment of the present invention.

Referring to FIGS. 1 and 2, the compact pipe specimen 100 comprises the cylindrical specimen 110 having a hollow portion and the first and second jigs 120 and 130 that are directly attached to the exterior surface of the pipe 110.

A notch portion 112 is formed in the pipe 110 in a circumferential direction. A crack portion 114 is formed on the edge of the notch portion 112. A bending load is applied to the crack portion 114 when a fracture toughness test of a pipe material is conducted. Meanwhile, since the pipe 110 is the same as an actually used pipe, it is not required to correct the influence of a constraint effect due to varying sizes and shapes of a pipe.

Thereafter, the first jig 120 and the second jig 130 are attached to the pipe 110 above and below the notch portion 112 (in a direction of z) with the notch portion 112 of the pipe 110 therebetween, respectively. Two openings 122 and 132 are formed in the first and second jigs 120 and 130 to accommodate a pressurizing unit for generating the bending load, for example, a pin.

The first and second jigs 120 and 130 having the openings 122 and 132 are directly attached to the exterior surface of the pipe 110 so that a small load generated by pins can cause a large bending load. In more detail, an opening for accommodating a pin is formed in a conventional specimen, whereas the first and second jigs 120 and 130 are attached to the exterior surface of the pipe 110 and the openings 122 and 132 for accommodating a pin are formed in the first and second jigs 120 and 130, so that a location where the load generated by pins is applied is farther away from the center of the bending of the pipe 110 compared to the conventional specimen. Therefore, the small load generated by the pins can cause the large bending load on the pipe 110, and more specifically, on the crack portion 114.

Projections 124 and 134 are formed on the first and second jigs 120 and 130 toward the interior radial direction of the pipe 110. Two holes 118 are formed in the exterior surface of the pipe 110 so as to accommodate the projections 124 and 134. In more detail, the two holes 118 are formed in a vertical direction (in a direction of z in drawings) with the notch portion 112 therebetween, respectively. The holes 118 are formed to pass through the pipe 110 in a radial direction. The sizes of the holes 118 correspond to those of the cross-sections of the projections 124 and 134 so that the projection 124 of the first jig 120 is accommodated by the hole 118 formed in the upper portion of the notch portion 112, and the projection 134 of the second jig 130 is accommodated by the hole 118 formed in the lower portion of the notch portion 112.

The projections 124 and 134 are formed on the first and second jigs 120 and 130 and the holes 118 are formed in the exterior surface of the pipe 110, thereby directly attaching the first and second jigs 120 and 130 to the exterior surface of the pipe 110 without influencing the curvature of the pipe 110.

The projections 124 and 134 may be more tightly coupled to the pipe 110 by using engagement units. In more detail, end portions of the projections 124 and 134 are processed into nuts (not shown) and the pipe 110 includes two washers 128 and 138 and two bolts 126 and 136 inside the pipe 110, so that the end portions of the projections 124 and 134 that are inserted into the pipe 110 through the holes 118 are coupled to engagement units, such as the washers 128 and 138 and the bolts 126 and 136 (see FIG. 2), thereby more tightly attaching the first and second jigs 120 and 130 to the exterior surface of the pipe 110. The exterior surfaces of the washers 128 and 138 that contact the interior surfaces of the pipe 110 are processed to have a curvature corresponding to the interior curvature of the pipe 110, so that the first and second jigs 120 and 130 can be more stably attached to the exterior surface of the pipe 110.

Figure 3:
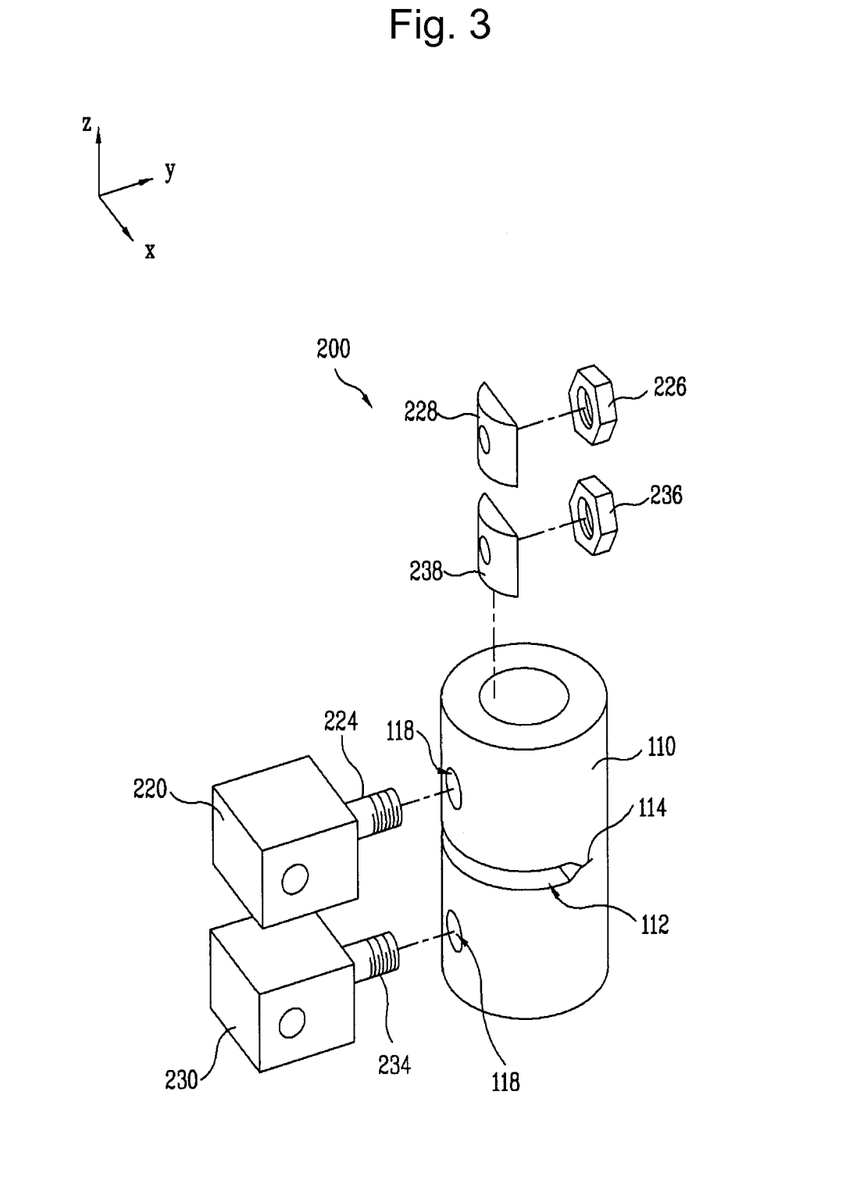
FIG. 3 is an exploded perspective view of a compact pipe specimen having a pipe and first and second jigs that are separated from each other according to another embodiment of the present invention.

FIG. 3 is an exploded perspective view of a compact pipe specimen 200 having the pipe 110 and first and second jigs 220 and 230 that are separated from each other according to an embodiment of the present invention.

Referring to FIG. 3, the compact pipe specimen 200 of the present embodiment is different from the compact pipe specimen 100 shown in FIG. 1 in that end portions of projections 224 and 234 of the first and second jigs 220 and 230 are processed into bolts. The pipe 110 includes two washers 228 and 238 and two nuts 226 and 236 as engagement units inside the pipe 110, so that the end portions of the projections 224 and 234 that are inserted into the pipe 110 through the holes 118 are coupled by, respectively, the washers 228 and 238 and the bolts 226 and 236, thereby more tightly attaching the first and second jigs 220 and 230 to the exterior surface of the pipe 110.

Although the end portions of the projections 124, 134, 224, and 234 and the engagement units are coupled to each other as bolts and nuts in the embodiments with reference to FIGS. 1 through 3, the present invention is not limited thereto and a combination of various shapes of jigs and engagement units that can be attached to the exterior surfaces of the pipe 110 may be possible and within the scope of the present invention.

Figure 4:
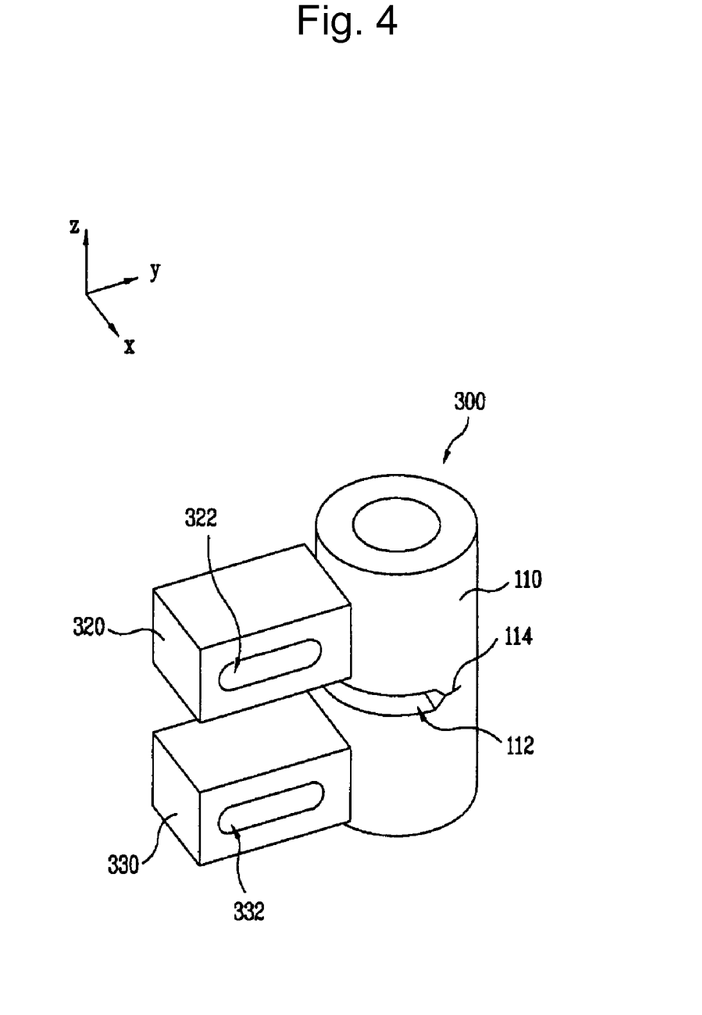
FIG. 4 is a perspective view of a compact pipe specimen according to another embodiment of the present invention.

FIG. 4 is a perspective view of a compact pipe specimen 300 according to another embodiment of the present invention.

Referring to FIG. 4, the arm lengths of a first jig 320 and a second jig 330 may be adjusted unlike those shown in FIGS. 1 through 3.

In more detail, the first and second jigs 320 and 330 are formed to be longer in a radial direction of the pipe 110 than those shown in FIGS. 1 through 3. Openings 322 and 332 formed in the first and second jigs 320 and 330 are formed as a slot extending in a lengthwise direction of the first and second jigs 320 and 330 (i.e., in an exterior radial direction from the exterior surface of the pipe 110). Pins coupled to the openings 322 and 332 may be secured at a predetermined location within the openings 322 and 332, which are in the form of slots, by using fixing units, such as nuts (not shown), so as to apply the load generated by the pins.

Therefore, a location where the load generated by the pins is applied is farther away from an axis that is the center of the bending of the pipe 110, so that a smaller load generated by the pins than that of FIGS. 1 through 3 can cause a large bending load on the crack portion 114.

In more detail, the fracture load of a pipe increases according to an increase in the thickness of the pipe in a radial direction of the pipe, which restricts the applicable pipe according to the capacity of a test device. However, according to the present embodiment, the arm lengths of the first and second jigs 320 and 330 are adjusted according to the thickness of the pipe in the radial direction of the pipe, thereby conducting a pipe test by using a test device with a relatively small capacity, despite the increase in the thickness of the pipe.

Although the slot-shaped openings 322 and 332 are formed in the first and second jigs 320 and 330 in order to adjust the arm lengths of the first and second jigs 320 and 330 in the present embodiment, the present invention is not limited thereto and a combination of various shapes of jigs and openings may be possible, which is within the scope of the present invention. For example, the circular shaped openings 122 and 132 may be spaced apart from each other by a predetermined interval in a lengthwise direction of the first and second jigs 120 and 130 or circular shaped openings may be formed in a plurality of jigs in a variety of locations in the lengthwise direction of the jigs.

Figure 5:
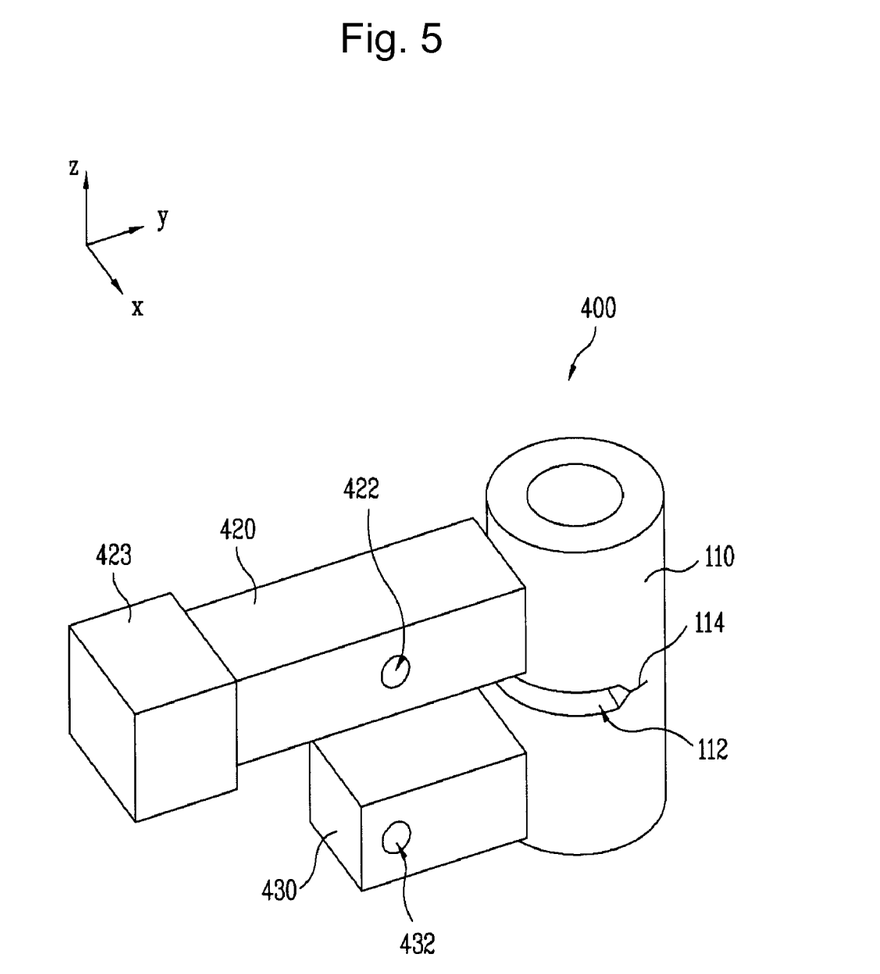
FIG. 5 is a perspective view of a compact pipe specimen according to another embodiment of the present invention.

FIG. 5 is a perspective view of a compact pipe specimen 400 according to another embodiment of the present invention.

Referring to FIG. 5, a weight 423 is formed at an edge portion of a first jig 420 unlike those shown in FIGS. 1 through 4.

In more detail, if the size and thickness of a pipe increase, when the compact pipe specimen 400 is installed in a test device, the compact pipe specimen 400 may incline to the pipe due to the weight of the pipe (in a right lower direction from an opening 422 in which a pin is accommodated in FIG. 5). When the compact pipe specimen 400 inclines, a side force is applied to the test device, so that the jigs and the pipe cannot be disposed in parallel to the test device, and thus a load is applied to the test device. However, in the present embodiment, the weight 423 corresponding to the weight of the pipe is coupled to the first jig 420 on the opposite to the pipe 110 (i.e., on the left of the opening 422 in which the pin is accommodated in FIG. 5), thereby protecting the test device from being burdened and preventing the compact pipe specimen 400 from inclining due to the weight of the pipe.

Meanwhile, although the weight 423 is attached to the edge of the compact pipe specimen 400 in the present embodiment, the weight 423 may move on the first jig 420 horizontally. In this case, although the weight of the pipe may vary, the varying weight of the pipe may be corrected by moving the weight 423 horizontally.

Figure 6:
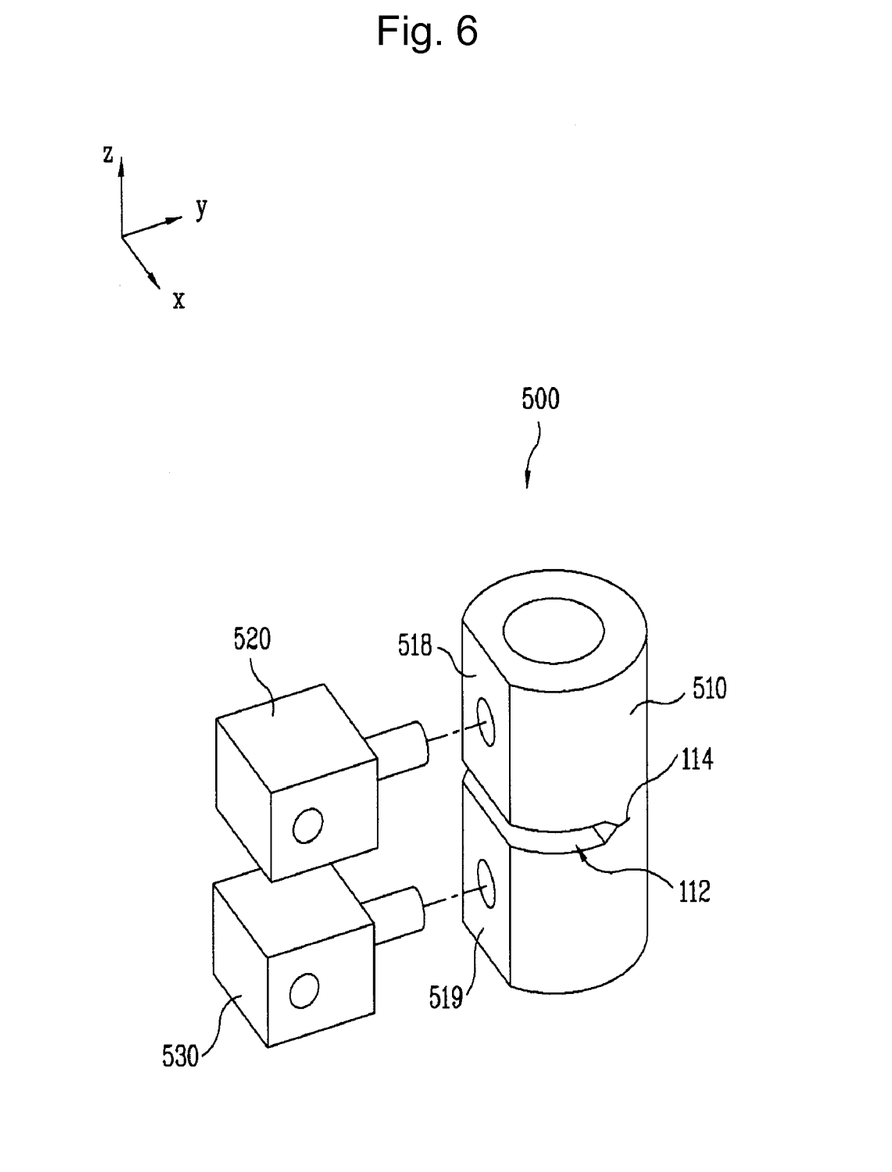
FIG. 6 is a perspective view of a compact pipe specimen according to another embodiment of the present invention.

FIG. 6 is a perspective view of a compact pipe specimen 500 according to another embodiment of the present invention.

Referring to FIG. 6, the exterior surface of a pipe 510 is partially planar unlike the exterior surfaces shown in FIGS. 1 through 5.

In more detail, planar portions 518 and 519 are formed on the exterior surface of the pipe 510 facing first and second jigs 520 and 530 so that the first jig 520 is attached to the planar portion 518 disposed on the upper portion of the notch portion 112 and the second jig 530 is attached to the planar portion 519 disposed on the lower portion of the notch portion 112.

The planar portions 518 and 519 are formed on the exterior surface of the pipe 510, thereby stably and easily attaching the first and second jigs 520 and 530 to the exterior surface of the pipe 510.

Although the exterior surface of the pipe 510 is partially planar in the present embodiment, the present invention is not limited thereto and the exterior surface of the pipe may be curved according to the shape of the exterior surface of the first and second jigs attached to the pipe, which is within the scope of the present invention.

Although the exterior surface of the pipe 510 is partially planar in the present embodiment, the present invention is not limited thereto and the exterior surface of the first and second jigs may be processed to correspond to the curvature of the exterior surface of the pipe 510 attached to the first and second jigs, which is within the scope of the present invention. In more detail, the exterior surface of one of the pipe and the first and second jigs may be processed so that the pipe and the first and second jigs contact each other, thereby more easily attaching the first and second jigs to the pipe.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

According to the compact pipe specimen of the present invention, it is unnecessary to correct the influence of a constraint effect due to varying sizes and shapes of a pipe, the specimen can be directly extracted from the pipe, the curvature and thickness of the pipe are not restricted, and thus, a fracture characteristic value with regard to pipes having various curvatures and thicknesses can be obtained. Furthermore, test equipment can be minimized and simplified compared to the conventional specimen, which reduces equipment costs, and a test can be conducted in a laboratory environment, making it possible to conduct the test at a high temperature that is similar to actual operating conditions of a nuclear reactor, for example.

The invention claimed is:

1. A compact pipe specimen applicable to a fracture toughness test of a pipe material, the compact pipe specimen comprising:
    a pipe which is cylindrical and has a hollow portion, the pipe having a notch portion formed in a circumferential direction and a crack portion formed at the edge of the notch portion; and
    first and second jigs having openings to which a pressurizing unit is coupled so as to cause a bending load on the pipe, having the notch portion therebetween, and attached to the exterior surface of the pipe, respectively,
    wherein projections are formed toward the pipe on the first and second jigs that are attached to the pipe, respectively,
    wherein holes are formed in the pipe, pass through the pipe in a radial direction of the pipe, and have sizes corresponding to the cross-sections of the projections, and
    wherein the projections are coupled to the holes so that the first and second jigs are attached to the exterior surface of the pipe, respectively.

2. The compact pipe specimen of claim 1, wherein the arm lengths of the first and second jigs are adjusted according to the thickness of the pipe in the radial direction of the pipe.

3. The compact pipe specimen of claim 2, wherein the openings are in the form of slots extending in a lengthwise direction of the first and second jigs.

4. The compact pipe specimen of claim 2, wherein end portions of the projections coupled to the holes are coupled to engagement units inside the pipe.

5. The compact pipe specimen of claim 4, wherein the engagement units include washers and bolts, and wherein the end portions of the projections are processed into nuts and are coupled to the washers and bolts.

6. The compact pipe specimen of claim 4, wherein the engagement units include washers and nuts, and wherein the end portions of the projections are processed into bolts and are coupled to the washers and nuts.

7. The compact pipe specimen of claim 2, wherein a weight is attached to the edge of the first jig or the second jig.

8. The compact pipe specimen of claim 2, wherein the exterior surface of at least one of the first and second jigs and the pipe is processed so that the first jig and the pipe or the second jig and the pipe have contact surfaces matching each other.

9. The compact pipe specimen of claim 8, wherein a plane portion is formed on the exterior surface of the pipe to which the first jig or the second jig is attached.

10. The compact pipe specimen of claim 1, wherein end portions of the projections coupled to the holes are coupled to engagement units inside the pipe.

11. The compact pipe specimen of claim 10, wherein the engagement units include washers and bolts, and wherein the end portions of the projections are processed into nuts and are coupled to the washers and bolts.

12. The compact pipe specimen of claim 10, wherein the engagement units include washers and nuts, and wherein the end portions of the projections are processed into bolts and are coupled to the washers and nuts.

13. The compact pipe specimen of claim 1, wherein a weight is attached to the edge of the first jig or the second jig.

14. The compact pipe specimen of claim 1, wherein the exterior surface of at least one of the first and second jigs and the pipe is processed so that the first jig and the pipe or the second jig and the pipe have contact surfaces matching each other.

15. The compact pipe specimen of claim 14, wherein a plane portion is formed on the exterior surface of the pipe to which the first jig or the second jig is attached.

* * * * *